United States Patent [19]

Centifanto

[11] Patent Number: 5,232,700
[45] Date of Patent: Aug. 3, 1993

[54] METHODS OF PROPHYLAXIS AND TREATMENT OF HERPES SIMPLEX LESIONS UTILIZING PIRACETAM AS THE ACTIVE INGREDIENT

[75] Inventor: Ysolina Centifanto, Metairie, La.

[73] Assignee: The Administrators of the Tulane Educational Fund, New Orleans, La.

[21] Appl. No.: 613,419

[22] Filed: Nov. 14, 1990

[51] Int. Cl.⁵ .............................................. A61K 09/06
[52] U.S. Cl. ..................................... 424/400; 424/427;
514/912; 514/914; 514/931; 514/934
[58] Field of Search .............. 424/401, 433; 514/931,
514/934, 967, 969

[56] References Cited

U.S. PATENT DOCUMENTS

| | | | |
|---|---|---|---|
| 4,513,008 | 4/1985 | Revici et al. | 514/560 |
| 4,534,959 | 8/1985 | Schmolka | 424/45 |
| 4,620,973 | 11/1986 | Truog | 424/10 |
| 4,728,605 | 3/1988 | Fudenberg et al. | 435/29 |
| 4,789,669 | 12/1988 | Sugimoto et al. | 514/178 |
| 4,952,560 | 8/1990 | Kigasawa et al. | 514/2 |

OTHER PUBLICATIONS

Niss et al., Efficacy of Piracetam Treatment of Acute Viral Neuroinfections, Zh Nevropatol Psikhiatr. 1985, 85(2) pp. 189-195 ISSN 0044-4588, abstract provided.
Karacostas et al., Piracetam for the Treatment of Myoclonus Secondary to Herpes Simplex Encephalitis Case Report, Acta Therapeutica 14(3) 1988 pp. 293-299, abstract provided.

Primary Examiner—Thurman K. Page
Assistant Examiner—Robert H. Harrison
Attorney, Agent, or Firm—Pennie & Edmonds

[57] ABSTRACT

A piracetam-containing preparation is applied to prevent and/or treat recurrent herpetic lesions. When used prophylactically, the piracetam-containing preparation is applied during the prodromal phase of a herpes recurrence at the site of previous eruptions. When used for treatment purposes, the piracetam-containing preparation is initially applied within six to twelve hours of the appearance of the herpetic lesions and application is continued at set intervals until the lesions disappear.

8 Claims, 6 Drawing Sheets

METHODS OF PROPHYLAXIS AND TREATMENT OF HERPES SIMPLEX LESIONS UTILIZING PIRACETAM AS THE ACTIVE INGREDIENT

TABLE OF CONTENTS

1. Introduction
2. Background Of The Invention
3. Summary Of The Invention
4. Description Of The Figures
5. Detail Description Of The Invention
    5.1 Preparation Of Piracetam Ointment
    5.2 Non-Oncogenicity Of Piracetam Ointment
    5.3 Prophylaxis And Therapy Of HSV Lesions In Humans
6. In Vitro Studies
    6.1 Growth Of Cells
    6.2 Plaque Inhibition Assay
    6.3 Electron Microscopy
    6.4 Effect Of Piracetam On Non-Infected Cells
    6.5 Effect of Piracetam On HSV-1 Infected Cells
    6.6 Mode Of Action
7. In Vivo Animal Studies
    7.1 The Guinea Pig Model
    7.2 Primary Disease Experiments
    7.3 Recurrent Disease Experiments

1. INTRODUCTION

The present invention is directed to the topical application of a piracetam (2 oxo-1-pyrrodiline acetamide) ointment to prevent recurrent lesions associated with Herpes Simplex Virus (HSV) infection. In a specific embodiment of the invention, a piracetam ointment is prophylactically applied to the skin to prevent the formation of recurrent herpetic lesions. In another embodiment, a piracetam ointment is applied within six to twelve hours of the appearance of cutaneous lesions to reduce the number, size and duration of the lesions formed. In a different embodiment of the invention, a piracetam ointment, suitable for ocular administration, is prophylactically applied to prevent recurrent herpetic infections of the eye. In another embodiment, the ocular piracetam ointment is applied as treatment of recurrent disease. In yet a different embodiment of the invention, a piracetam suppository is prophylactically inserted to prevent recurrent vaginal herpetic infections. In another embodiment, a vaginal piracetam suppository is applied as treatment of recurrent disease.

2. BACKGROUND OF THE INVENTION

There are two known strains of HSV: Herpes Simplex Virus Type 1 (HSV-1), which commonly causes herpes labialis (cold sores) and keratitis; and Herpes Simplex Virus Type 2 (HSV-2), which commonly causes genital herpes. The time of initial herpes infection is often obscure and may pass unnoticed. A salient feature of HSV infections is the ability of the virus to remain dormant, most likely within the nervous system ganglia, and then be reactivated. Various factors are thought to trigger these recurrent herpetic episodes, including physical and/or emotional stress, overexposure to sunlight, and certain foods and drugs.

Upon reactivation, the latent HSV begins to replicate and then travels, via the axons, to a peripheral site, where it may shed asymptomatically or cause lesion formation. The differential conditions under which the reactivated virus causes lesions or is shed asymptomatically are not clear. However, asymptomatic shedding is thought to be a factor in the unchecked spread of herpetic diseases, particularly genital herpes.

An estimated 70–80% of the adult population in the United States shows antibodies to HSV-1, indicating past infection with the virus. Geographic location, socioeconomic status, and age, all influence the frequency of HSV. In Brazilian Indians, HSV antibodies are present in 95% of children by age 15. One study at a New Orleans clinic similarly revealed the presence of HSV antibodies in over 90% of children by age 15. Studies in Atlanta and Houston have shown 70–80% seroconversion by early adolescence [Rawls and Campione-Piccardo, Epidemiology of herpes simplex virus type 1 and 2 (1981) in "The Human Herpesvirus: An Interdisciplinary Perspective,"A. Nahmias, W. Dowdle and R. Schenazi, pp. 137–152,Elsevier, North Holland Amsterdam].

Infection with HSV-2 has become increasingly prevalent in the United States. "The estimated number of physician-patient consultations for genital herpes increased fifteen fold between 1966 and 1984, from 29,560 to 450,576. First Office visits—a more likely indicator of newly acquired infection—increased ninefold, from 17,810 in 1966, to 156,720 in 1984." ["Genital Herpes Infections," U.S. 1966-1984, Centers for Disease Control Morbid Mortal Weekly, Vol. 35:402, 1986]. Chronic, ulcerative, genital herpes is often seen in, and may be diagnostic of, individuals with Acquired Immune Deficiency Syndrome (AIDS).

Presently, HSV infections are treated with antiviral agents that interfere with viral replication. Stoxil (5-iodo-2deoxyuridine), Viroptic (trifluorothymidine), and Acyclovir (9-(2-Hydroxyethoxymethyl) guanine), all need to be incorporated into the viral DNA to exert their antiviral activity. [Kaufman H. E. Proc. Soc. Exp. Biol. Med. 109: 251–252 (1962); Elion G. B. et al. Proc. Natl. Acad. Sci. U.S.A. 74: 5716–5720 (1977); Shaeffer H.J. et al. Nature (London) 272: 583–585 (1978); Sugar J. et al. Invest. Ophthal. 12: 532 (1973); Wellings P. C. et al. Amer. J. Ophthal. 73: 932–42 (1972)].

Acyclovir, the current drug of choice for treating HSV, is available in intravenous (IV), topical and oral forms. However, it is most effective in treating primary herpetic infections and is less effective in either preventing or treating recurrent infections [Bryson Y. J. et al. New Engl. J. Med. 308: 916–921 (1983); Mertz G. J. et al. J. Amer. Med. Assoc. 252: 1147–1151 (1984)]. Continuous administration of acyclovir suppresses the number of recurrences, but the frequency of recurrences reverts to its original status when the drug is discontinued [Douglas J. M. et al. New Engl. J. Med. 310: 1551–1556 (1984); Kinghorn G. C. et al. Gentourin. Med. 61: 387–390 (1985); Straus S .E. et al. New Engl. J. Med. 310: 1545–1550 (1984)].

Drugs are also known which suppress viral growth by mechanisms other than those which directly interfere with viral DNA. Smooth muscle relaxing agents, such as Verapamil and Papaverine have been shown to inhibit the replication of cytomegalovirus and influenzae virus

[Albrecht T. et al. Proc. Soc. Exp. Bio. Med. 186: 41–46 (1987); Nugent K. M. et al. Archives of Virology 81: 163-170 (1984)]. Non-steroidal anti-inflammatory drugs are known to inhibit the multiplication of several viruses, including Sindbis, Influenzae A2, HSV, and vaccinia [Inglot A. D. Comparison of the antiviral activity in vitro of some non-steroidal drugs. J. Gen.

Virol. 4: 203–214 (1969)]. Lithium, a psychoactive drug, has been found to cause the remission of HSV infections in patients under systemic treatment [Lieb J. New Engl. J. Med. 301: 942 (1979); Trousdale M. D. et al. Antimicrob. Agents Chemother. 25: 522–523 (1984)]. Subsequently, lithium succinate was used as a topical treatment for genital herpes [Skinner G. R. B. The Lancet 2: 288 (1983)]. Most recently, orally administered piracetam was observed to affect beneficially the outcome of myoclonus in an individual with herpes simplex encephalitis. [Karacostas D. et al. Acta Therapeutica 14: 293–299 (1988)].

3. SUMMARY OF THE INVENTION

The present invention is directed to the topical application of a piracetam ointment or suppository to prevent and/or treat the cutaneous manifestations of recurrent herpetic infections.

The invention is based, in part, on the discovery that reactivation at the ganglionic site and lesion formation are two independent phenomena, with different regulatory mechanisms [Centifanto Y.M. et al. Proc. Soc. Exp Biol. Med. 185: 484–492 (1987)] and that the prevention of lesion formation requires a different approach from that conventionally directed against viral replication. More specifically, the present invention is based, in part, on the surprising discovery that lesion formation may be prevented and/or interrupted without interfering with the viral DNA or replication cycle. The method of the present invention thus provides distinct advantages over present modes of treatment. Since the mode of action of piracetam is not based on the incorporation of the drug into the viral DNA, the emergence of drug resistant strains and the risk of oncogenicity are eliminated.

5. DETAILED DESCRIPTION OF THE INVENTION

Topically applied piracetam is advantageously used for prophylactic and/or therapeutic treatment of the cutaneous manifestations of recurrent Herpes virus infections.

5.1 PREPARATION OF PIRACETAM OINTMENT

Suitable ointments for application to human skin would include Carbowax Base II and Emulsifiable Glycol Ointment Base G, as described in Remington's *Practice of Pharmacy* Martin and Cook (Ed.), 1962, in which is dissolved a therapeutically effective amount of piracetam, preferably about 5–10%.

For ocular application, a therapeutically effective amount of piracetam, preferably about 5–10%, is dissolved in an ointment known to be suitable for ocular application in humans.

A therapeutically effective amount of piracetam, preferably about 5–10% may also be incorporated into known vaginal suppository formulations.

5.2 NON-ONCOGENICITY OF PIRACETAM PREPARATIONS

Since the mode of action of piracetam is not based on the incorporation of the drug into the viral DNA, the emergence of drug resistant strains and the risk of oncogenicity are eliminated.

5.3 PROPHYLAXIS AND THERAPY OF HSV LESIONS IN HUMANS

Within six to twelve hours of the appearance of herpetic lesions, a piracetam ointment, prepared as described in section 5.1, is applied to all lesions. Ointment is applied every 2–3 hours thereafter, for a total of at least six applications per day. Treatment is to be continued until the lesions disappear. For maximum benefits, therapy should be initiated during the prodromal phase of the disease, before the appearance of lesions. The ointment should be applied to sites where lesions are expected to recur, i.e., the sites of previous eruptions.

The following series of Examples are presented for purposes of illustration and not by way of limitation on the scope of the invention.

6. IN VITRO STUDIES

Piracetam's effectiveness as an anti-viral agent was assessed with in vitro studies.

6.1 GROWTH OF CELLS

Vero cells were grown in Eagle's basal minimal medium supplemented with 10–15% fetal calf serum, 1% glutamine, sodium bicarbonate and antibiotics.

6.2 PLAQUE INHIBITION ASSAY

The effectiveness of piracetam as an antiviral agent was determined by plaque inhibition assays. Monolayer cultures of Vero cells in 35 mm wells were infected with the appropriate amount of HSV-1 McKrae strain and allowed to adsorb for forty-five minutes at 37° C. After this period, maintenance medium (consisting of a balanced salt solution supplemented with 2% calf serum, glutamine, sodium bicarbonate and antibiotics), with or without piracetam, was added, and the cultures were incubated for an additional 36 to 48 hours to allow the formation of discrete, well-formed plaques which could be counted. The cultures were then stained with crystal violet, and the plaques counted.

6.3 ELECTRON MICROSCOPY

For transmission electron microscopy, the Vero cells were first harvested and centrifuged. Pellets were then cut and double fixed in 2.5% glutaraldehyde and 1% osmium teroxide. As a final step, the pellets were dehydrated in graded alcohol and embedded in Epon 812. One micron-thick sections from each pellet were stained with toluidine blue and examined with a light microscope under standard conditions. Thin sections were cut from selected areas that comprised both infected and uninfected cells. Photographs were taken with an EM-109 (Carl Zeiss, Inc., West Germany) microscope under standard conditions.

6.4 EFFECT OF PIRACETAM ON NON-INFECTED CELLS

As one control, the effect of piracetam on non-infected cells was tested as follows. Confluent monolayers of Vero cells were overlaid with maintenance media containing different concentrations of the drug. Piracetam, at concentrations of 20 mg, 2 mg, 200 µg, 20 µg, and 2 µg per milliliter, was placed over the monolayer at twenty-four hours. The medium without the drug was placed over the monolayer for an additional twenty-four hours. The plates were then washed, and their appearances, as compared to non-drug controls, were recorded. Piracetam, at the specified concentrations, was not found to have any detrimental effect on the cells, e g "lifting off" from the plastic (an indication of cell death), though a slight, but reversible, thinning of the monolayer was observed at 20 mg/ml. After further incubation of the cells with fresh maintenance media, all cells appeared normal and no differences were observed between drug-treated and non-drug-treated cells.

6.5 EFFECT OF PIRACETAM ON HSV-1 INFECTED CELLS

The anti-viral effectiveness of piracetam was demonstrated by testing the effect of the drug on HSV-1 infected cells. Vero cell monolayers were infected with an appropriate amount of the HSV-1 McKrae strain. After an adsorption period of about forty-five minutes, the monolayers were overlaid with maintenance media containing piracetam at concentrations of 20 mg, 2 mg, 200 µg, 20 µg and 2 µg per milliliter. The plates were incubated at 37° C. in a humidified 5% $CO_2$ atmosphere for approximately thirty-six to forty-eight hours until plaques were visible, and then stained with crystal violet when discrete, well-formed plaques were seen in the non-drug-treated control cultures. As shown in Table 1, no plaques were observed on cultures containing 20 mg/ml piracetam. The remaining cultures contained an average of 185 HSV plaques per well, a number similar to that of the non-drug-treated control cultures. The various drug-treated plaques showed no significant variation in the number of plaques per well.

TABLE 1

| Inhibitory effect of Piracetam on replication of HSV-1 in Vero cell cultures | |
|---|---|
| mg/ml | PFU/well* |
| 20 | 0 |
| 2 | 185 |
| 0.2 | 183 |
| 0.02 | 186 |
| 0.002 | 184 |

TABLE 1-continued

| Inhibitory effect of Piracetam on replication of HSV-1 in Vero cell cultures | |
|---|---|
| mg/ml | PFU/well* |
| VC | 185 |

VC = virus control
*average of four counts on duplicate cultures

Since inhibition of HSV-1 replication either occurred as a total phenomenon at 20 mg/ml, or did not occur at all, the time-course of the appearance of inhibition was determined. Vero cell cultures were infected with the HSV-1 McKrae strain as described. Piracetam at 20 mg/ml was added to the cultures at the following intervals: 1) just after virus adsorption, i.e., forty-five minutes after infection (a time period observed to be sufficient to permit the majority of virus particles to attach to the cell membrane and commence penetration) 2) six hours after virus adsorption, and 3) twenty-four hours after virus adsorption. In another set of cultures, the drug was removed by aspiration at six hours and at twenty-four hours post-infection, as measured from the time the virus suspension was placed on the monolayer. As shown in Table 2, 20 mg/ml of piracetam, added to the cultures after virus adsorption, effectively inhibited plaque formation. The same concentration of piracetam added six hours after adsorption also inhibited plaque formation. However, the addition of piracetam twenty-four hours post-infection did not affect the number of HSV plaques, as compared with non-drug-treated control cultures. Removal of the drug at six hours post-infection resulted in no inhibition of plaque formation. However, a 60% inhibition of plaque formation was seen when the drug was removed at twenty-four hours post-infection.

TABLE 2

| Inhibition of HSV-1 replication by piracetam in Vero cell cultures | |
|---|---|
| Piracetam 20 mg/ml | PFU/well* |
| added at: | |
| 30 min p.i. | 0 |
| 6 hrs p.i. | 0 |
| 24 hrs p.i. | 175 |
| VC | 152 |
| removed at: | |
| 6 hrs p.i. | 160 |
| 24 hrs p.i. | 58 |
| VC | 157 |

VC = virus control
*average of four counts on duplicate cultures

6.6 MODE OF ACTION

Electron microscopy studies were undertaken to determine the mode of action of piracetam in cell culture. Vero cells infected with the HSV-1 McKrae strain were prepared and treated after virus adsorption, with 20 mg/ml piracetam in maintenance medium. Similar cultures in maintenance medium without the drug served as controls. The cells were embedded for electron microscopy work at T0 (after virus adsorption), T6 (six hours post-infection), and T24 (twenty-four hours post-infection). The samples were processed by standard procedures and observed with a Leitz electron microscope.

Figure 1:
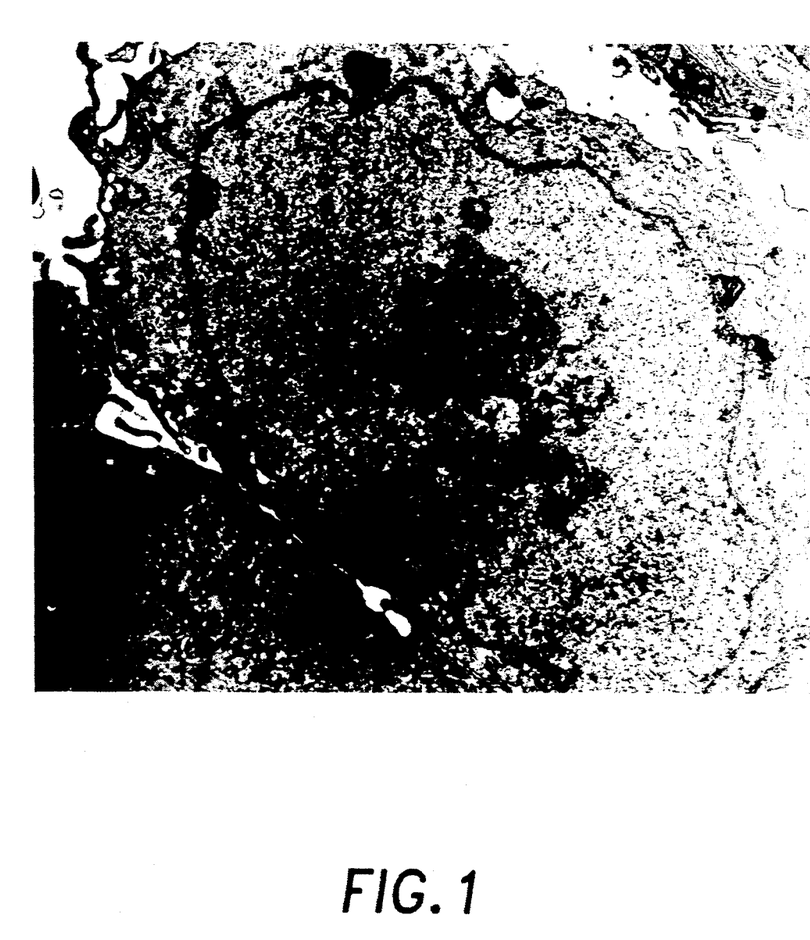
FIG. 1. Electron micrograph [Magnification ×15400] of Vero cells after six hours of infection with HSV McKrae strain. Some cells show intranuclear dense bodies of approximately 46–70 Angstroms in size.
Figure 2:
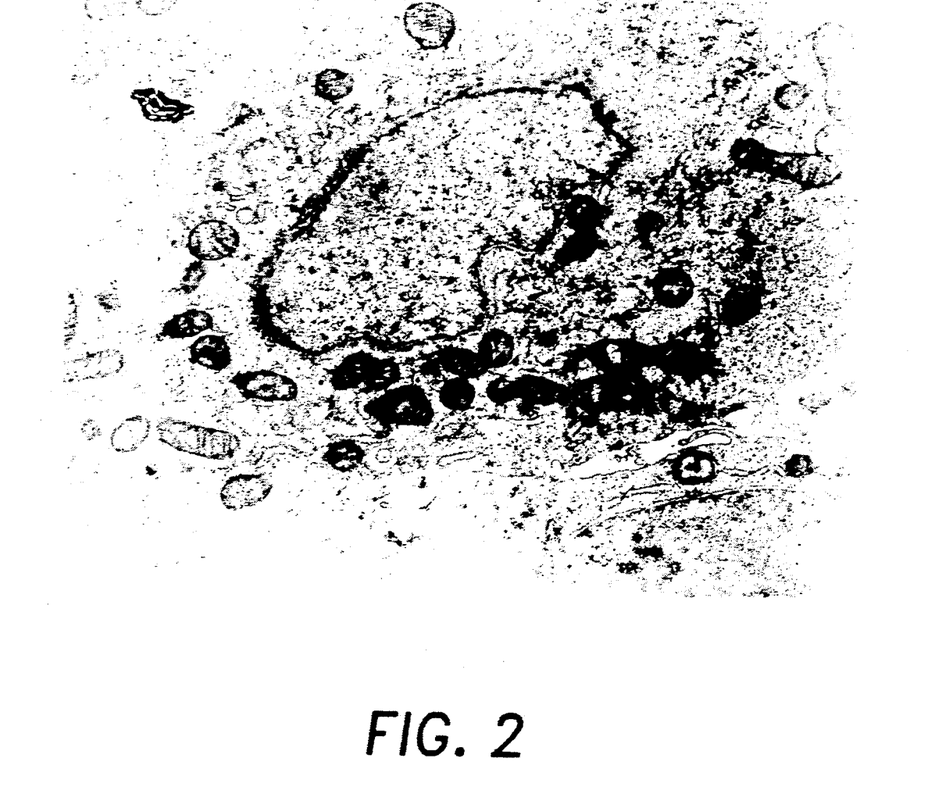
FIG. 2. Electron micrograph [Magnification ×17000] of piracetam-treated Vero cells after six hours of infection with HSV McKrae strain. A few intranuclear dense bodies of approximately 60 Angstroms in size, are observed.

The cells looked normal at T0, with no evident cytopathology. As shown in FIGS. 1 and 2, at T6, the infected cell, non-drug-treated controls showed numerous intranuclear dense bodies between 46 and 70 Angstroms in size. The same type of dense bodies were also found in the piracetam-treated cells. However, the number of cells containing such bodies was significantly lower than in the non-drug-treated control group.

Figure 3:
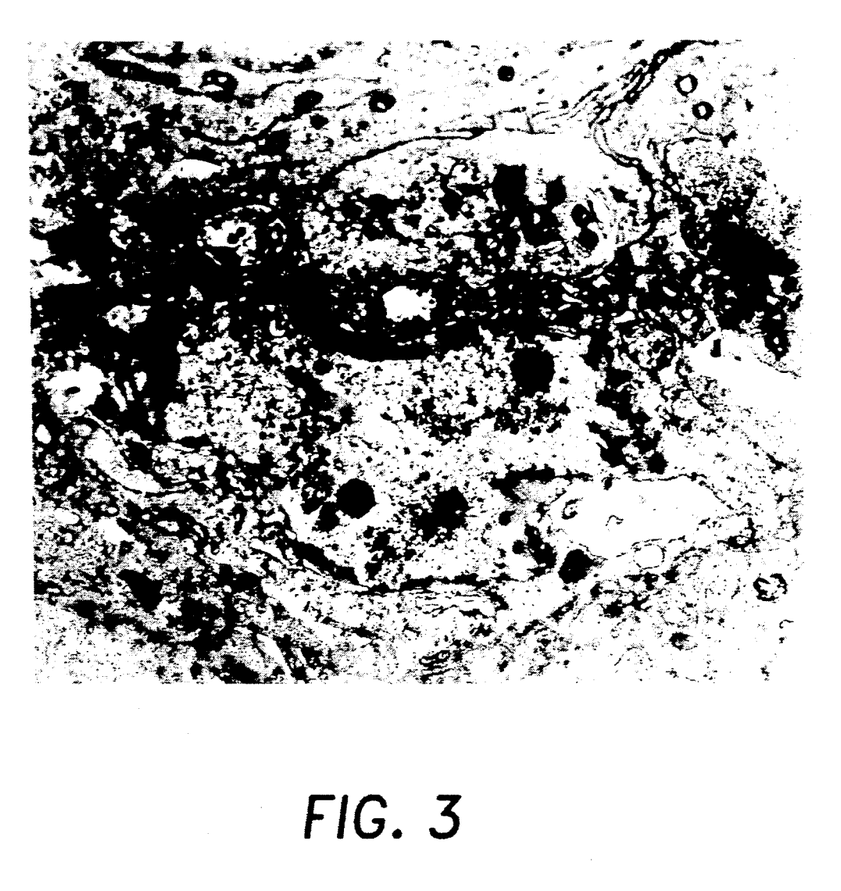
FIG. 3. Electron micrograph [Magnification ×22000] of non-piracetam treated Vero cells after twenty-four hours of infection with HSV McKrae strain. A large number of nucleocapsids are seen in the nucleus and virus particles are seen budding from the cytoplasm.
Figure 4:
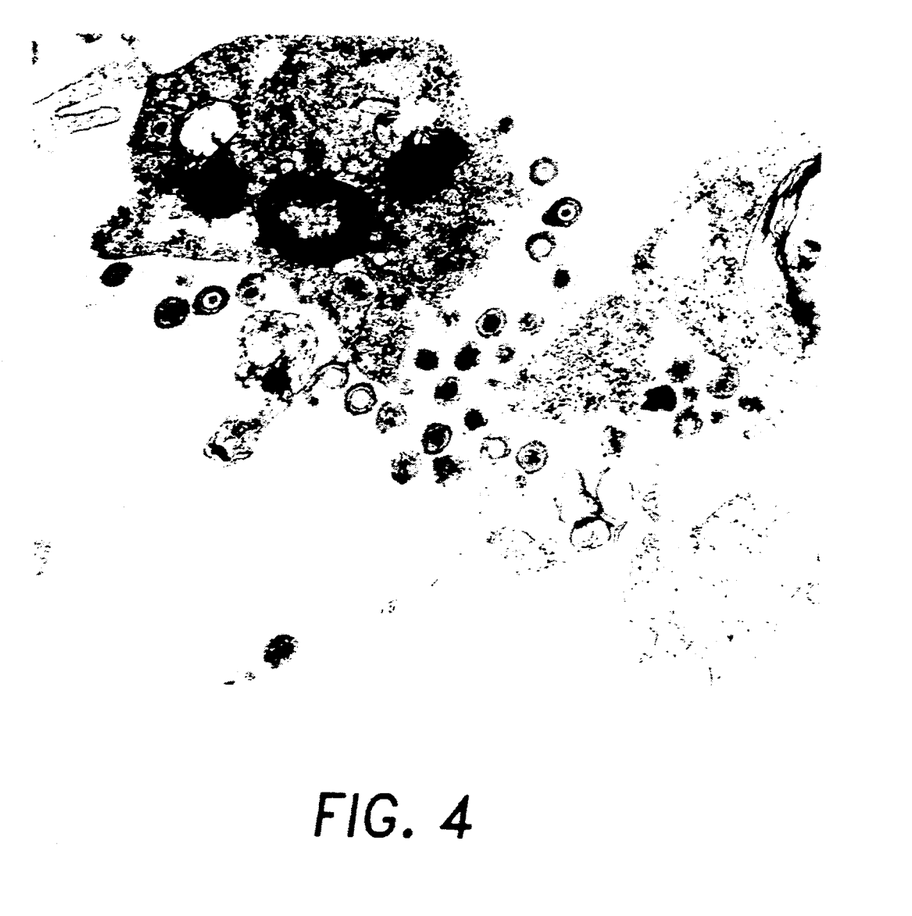
FIG. 4. Electron micrograph [Magnification ×22000] of non-piracetam treated Vero cells after twenty-four hours of infection with HSV McKrae strain. Many complete extracellular viral particles are seen.
Figure 5:
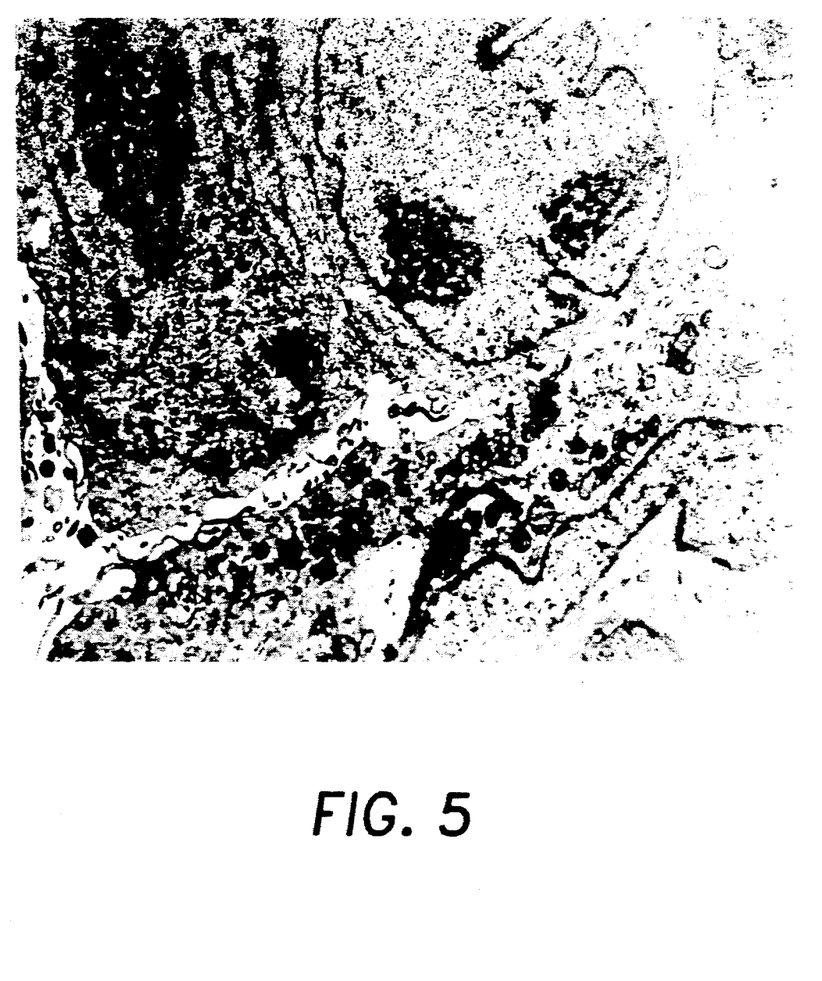
FIG. 5. Electron micrograph [Magnification × 27800] of piracetam-treated Vero cells after twenty-four hours of infection with HSV McKrae strain. No changes are seen in the cells and no virus particles are formed.

As shown in FIGS. 3, 4 and 5, dramatic differences were observed between the control and drug-treated groups at T24. In the infected, non-drug treated control group, complete virus particles were seen in the nuclei, cytoplasm, and extracellular spaces. In contrast, the piracetam-treated group showed no virus formation, and close examination of the cell showed no evidence of cytopathology. From this, the conclusion was made that the plaque inhibition seen earlier in the tissue culture experiments was due to the lack of formation of viral particles, a confirmation that no virus replication had taken place in the piracetam-treated cells.

A large number of cells were examined. As shown in Table 3, in the non-drug-treated control cultures at T24, 230 infected cells out of a total of 335 were observed. A large number of these cells showed both virus particles and intranuclear dense bodies. In contrast, the piracetam-treated cultures at T24 showed only 40 infected cells out of a total of 373 cells. The number of cells with intranuclear dense bodies was significantly lower, and no cells with complete virus particles were detected.

TABLE 3

Electron microscopy study of HSV-1 infected Vero cells treated with piracetam

| Group | Number of Cells Examined* | Number of cells with: Virus Particles | Number of cells with: Intranuclear Dense Bodies | Infected/ Total Cells |
| --- | --- | --- | --- | --- |
| Control T = 6 | 142 | | 21 | 44/280 |
| Treated T = 6 | 138 | | 23 | |
| | 138 | | 6 | |
| | 153 | | 7 | 13/291 |
| Control T = 24 | 149 | 55 | 59 | 230/335 |
| | 186 | 60 | 56 | |
| Treated T = 24 | 179 | $a$ | 14 | |
| | 194 | $4^b$ | 26 | 40/373 |

*Two fields counted
Confluent monolayer of Vero cells were infected with the HSV-1 McKrae strain. After virus adsorption, media with and without 20 mg/ml piracetam was added. At the designated times, 6 and 24 hours post-infection, both treated and untreated control cell cultures were harvested and processed for electronmicroscopy
$a$No virus particles detected.
$b$Defective virus particles only seen. No cells with complete virus particles detected.

7. IN VIVO ANIMAL STUDIES

7.1 The Guinea Pig Model

The anti-viral effectiveness of piracetam in vivo was demonstrated utilizing guinea pigs. The guinea pig model has been used extensively in the study and treatment of both genital and mucocutaneous herpetic lesions, of both HSV-1 and HSV-2 etiology [Kern, ER. "Treatment of genital herpes simplex virus infection in guinea pigs." F. Rapp (Ed.), Herpesvirus, pp. 617-636. Liss, New York: 1984; Stanberry, LR. J. Med. Virol. 28: 125-128 (1989)]. Because of the similarity of herpetic disease in guinea pigs and humans, the guinea pig model has proven useful for testing antiviral drugs [Luby JP et al. J. Infect. Dis. 150: 1-6 (1984); Nilsen AE et al. Lancet ii: 571-573 (1982)]. As further evidence of the usefulness of the guinea pig model, several of the experimental procedures used in these animals for the reactivation of the herpes virus and subsequent appearance of recurrent disease, have now been applied to humans [Spruance SL. Am. J. Med. 85(supp. 2A): 43-45 (1988); Spruance SL. J. Clin. Microbiol. 22: 366-368 (1985); Spruance SL et al. J. Am. Med. Assoc. 260: 1597-599 (1988); Perna JJ et al. J. Am. Acad. Dermatol. 17: 473-478 (1987)].

7.2 PRIMARY DISEASE EXPERIMENTS

Hartley guinea pigs (300-500 g), obtained from Charles River Laboratories (Newfield, New Jersey) were anesthetized with 0.5 ml of a Ketamine-Rompun mixture. The right and left shoulder and flank areas were shaved with electric clippers and denuded with the aid of a depilatory cream. The areas were washed and dried thoroughly prior to infection. Approximately 60 $\mu$l of a virus stock, either HSV-1 SC-16 strain ($5 \times 10^6$ plaque forming units [PFU]) or HSV-2 (333) strain was applied to each field and then inoculated with a six-needle head, spring-loaded, multiple-puncture apparatus (Bignrell, Sussex, England). In each field, the instrument was triggered ten times to a depth of 0.75 mm. The animals were examined daily for a period of 8 to 10 days for the HSV-1 infected animals and 3-5 days for the HSV-2 infected animals, and the lesions were counted and photographed.

In the first series of experiments, 5% piracetam was dissolved in a glycerin-petroleum jelly mixture and applied to the infected areas four times per day. The animals were examined daily, under an operating microscope, for lesions. The piracetam-treated animals exhibited less disease, as determined either by the total number of lesions or from the average number of lesions per infected area. The inhibition of lesion formation in HSV-1 infected animals ranged from 40 to 52% as compared to the control animals. In HSV-2 infected animals, about 41% inhibition of lesion formation was observed. Similar results were obtained in HSV-1 infected animals when piracetam was suspended in sesame oil.

7.3 RECURRENT DISEASE EXPERIMENTS

Figure 6:
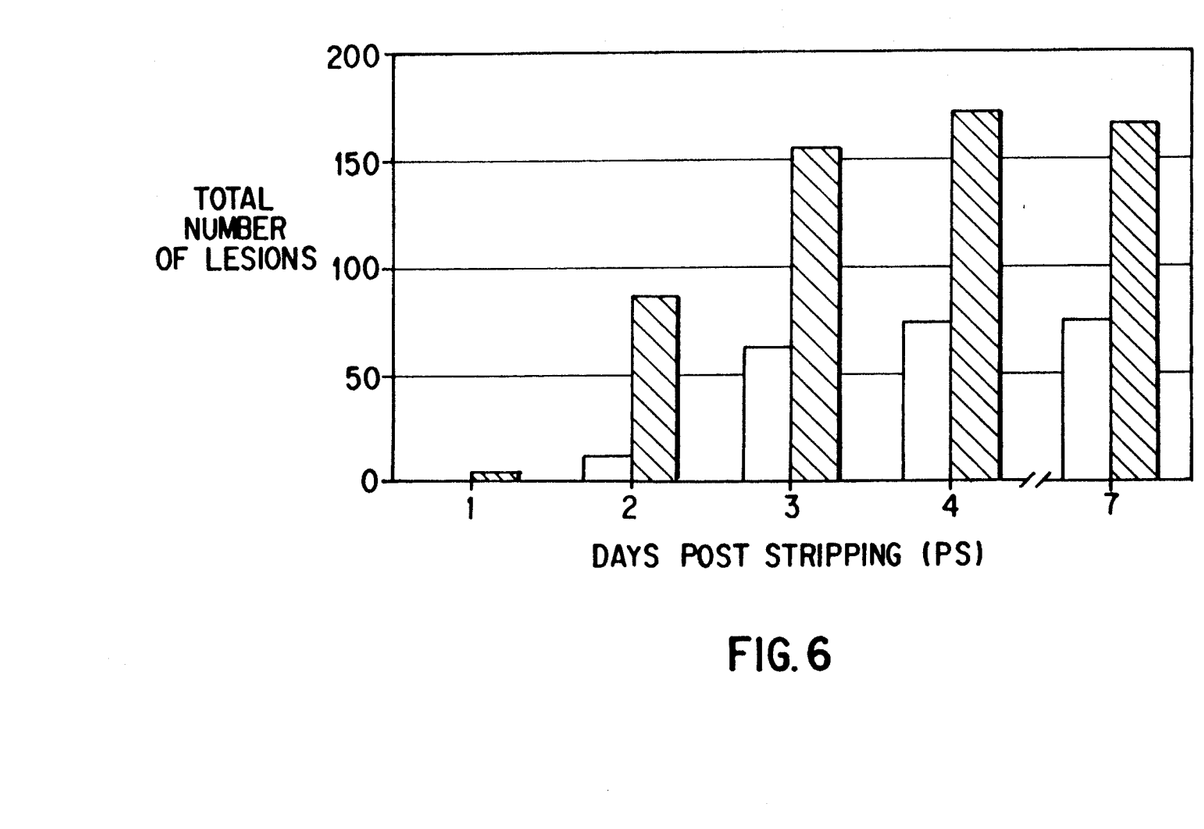
FIG. 6. Bar graph showing inhibitory effect of piracetam on number of recurrent lesions in guinea pigs infected with HSV-1.

Nude VAF guinea pigs previously infected with HSV-1 SC-16 strain which was now in the latent state, were stripped with cellophane tape to induce recurrent episodes of herpetic disease. The animals were treated six times a day, starting one hour after stripping, with piracetam dissolved in lecithin as the drug vehicle. As shown in FIG. 6, the inhibition of lesion formation was recorded to be 85% to 54% through days 1-6 post-stripping. Not only was the number of lesions fewer, but their size was smaller, no crust formation was seen, and the lesions were readsorbed faster than those seen on the control animals.

The present invention is not to be limited in scope by the illustrative examples, since the examples are intended as illustrations of one aspect of the invention and functional equivalents are within the scope of this invention. Indeed, various modifications of the invention in addition to those shown and described herein will become apparent to those skilled in the art from the foregoing description and accompanying drawings. Such modifications are intended to fall within the scope of the appended claim.

What is claimed is:

1. A method for preventing the recurrence of herpetic lesions which comprises applying a topical preparation containing from about 5.0% to about 10.0% of piracetam.

2. The method according to claim 1 wherein the form of preparation is in an ointment that may be applied to the skin.

3. The method according to claim 1 wherein the preparation is in the form of an ointment that may be applied to the eyes.

4. The method according to claim 1 wherein the preparation is applied during the prodromal phase of a herpes recurrence.

5. The method according to claim 4, wherein the preparation is applied at the sites of previous eruptions.

6. A method for treating recurrent herpes which comprises a topical preparation containing from about 5.0% to about 10.0% piracetam initially applied topically within six to twelve hours after the appearance of herpetic lesions followed by topical application every two to three hours after the initial topical application for a total of at least six topical applications per day until the lesions disappear.

7. The method according to claim 7 wherein the preparation is in the form of an ointment that may be applied to the skin.

8. The method according to claim 7 wherein the preparation is in the form of an ointment that may be applied to the eyes.

* * * * *